(12) United States Patent
Vihvelin et al.

(10) Patent No.: US 10,559,981 B2
(45) Date of Patent: Feb. 11, 2020

(54) POWER LINKS AND METHODS FOR IMPROVED EFFICIENCY

(71) Applicant: Dalhousie University, Halifax (CA)

(72) Inventors: Hugo Vihvelin, Halifax (CA); Jeff Leadbetter, Dartmouth (CA); Manohar Bance, Halifax (CA); Robert B. A. Adamson, Halifax (CA); Jeremy A. Brown, Halifax (CA)

(73) Assignee: Daxsonics Ultrasound Inc., Halifax (CA)

( * ) Notice: Subject to any disclaimer, the term of this patent is extended or adjusted under 35 U.S.C. 154(b) by 10 days.

(21) Appl. No.: 15/320,980

(22) PCT Filed: Jun. 25, 2015

(86) PCT No.: PCT/CA2015/050588
§ 371 (c)(1),
(2) Date: Dec. 21, 2016

(87) PCT Pub. No.: WO2015/196290
PCT Pub. Date: Dec. 30, 2015

(65) Prior Publication Data
US 2017/0201131 A1    Jul. 13, 2017

Related U.S. Application Data

(60) Provisional application No. 62/017,145, filed on Jun. 25, 2014.

(51) Int. Cl.
*H02J 7/00* (2006.01)
*H02J 50/15* (2016.01)
*H02J 50/80* (2016.01)
*H02J 7/02* (2016.01)
*A61N 1/378* (2006.01)

(52) U.S. Cl.
CPC ............ *H02J 50/15* (2016.02); *A61N 1/3787* (2013.01); *H02J 7/025* (2013.01); *H02J 50/80* (2016.02)

(58) Field of Classification Search
CPC ........ H02J 7/025; H01F 38/14; Y02T 90/122; B60L 11/182; Y02E 60/12
USPC ......................................................... 320/108
See application file for complete search history.

(56) References Cited

U.S. PATENT DOCUMENTS

| 5,642,031 A | 6/1997 | Brotto | |
| 2010/0244580 A1* | 9/2010 | Uchida | .................. H02J 5/005 307/104 |
| 2012/0299540 A1 | 11/2012 | Perry | |

(Continued)

OTHER PUBLICATIONS

Shaul Ozeri, Doron Shmilovitz, Ultrasonic transcutaneous energy transfer for powering implanted devices, Ultrasonic 50 (2010) 556-566, 2009.

(Continued)

*Primary Examiner* — Arun C Williams
(74) *Attorney, Agent, or Firm* — Ryan W. Dupuis; Ade & Company Inc.; Kyle R. Satterthwaite

(57) ABSTRACT

Among other things, in general, methods of increasing transfer efficiency in a power link are described, as well as power links implementing such methods. Methods of dynamic charging are also described. Applications of such methods and power links include the charging of portable electronic devices as well as implantable medical devices.

4 Claims, 13 Drawing Sheets

(56) References Cited

U.S. PATENT DOCUMENTS

2012/0306265 A1* 12/2012 Yamamoto .............. B60L 5/005
 307/9.1
2013/0178915 A1  7/2013 Radziemski
2013/0271088 A1 10/2013 Hwang et al.
2014/0049422 A1*  2/2014 Von Novak ............. H02J 5/005
 342/146

OTHER PUBLICATIONS

Shaul, O.; Boaz, S.; Doron, S., Non-invastive sensing of the electrical energy harvested by medical implants powered by an ultrasonic transcutaneous energy transfer link, Industrial Elctronics (ISIE), 2012 IEEE International Symposium on, vol., No., pp. 1153,1157, May 28-31, 2012.

Sung Q Lee et al, "Biocompatible wireless power transferring based on ultrasonic resonance devices", Proceedings of meetings on acoustics, vol. 19 (1), May 31, 2013, Acoustical Society of America, US.

Leung Ho Fai et al, "Wireless electric power transfer based on Acoustic Energy through conductive media", 2014 9th IEEE Conference on Industrial Electronics and Applications, IEEE, Jun. 9, 2014, pp. 1555-1560, The University of Auckland, New Zealand.

* cited by examiner

POWER LINKS AND METHODS FOR IMPROVED EFFICIENCY

CROSS-REFERENCE TO RELATED APPLICATIONS

This application claims the benefit of U.S. Provisional Application 62/017,145, filed Jun. 25, 2014; the contents of which are hereby incorporated by reference.

BACKGROUND

Ultrasonic power transfer using piezoelectric devices is a promising wireless power transfer technology for a wide variety of charging use cases, including the charging of mobile devices and biomedical implants. Ultrasonic transcutaneous energy transfer (UTET) devices (also known as "power links") are a promising alternative to electromagnetic induction coils for providing power to devices across a medium such as water, air, or—as in the case of active implanted devices such as cochlear implants, pacemakers, and neurostimulators—through tissue. For many applications, UTET can provide power transfer efficiency and total power throughput comparable to magnetic induction coils, but in a much smaller and lighter device. Smaller power transfer devices could potentially benefit patients by providing an increase in the potential surgical sites for the implant unit, less surgical recessing, and increased comfort and aesthetic appeal for device users. Smaller devices may also use smaller alignment magnets, which may increase MRI compatibility for the implant.

However, power transfer efficiency (PTE) tests reveal a challenge in the design of UTET systems, as efficiency levels show extreme sensitivity to the transmitting frequency and the acoustic separation distance between the transmitting and receiving piezoelectric transducers. PTE sensitivity is a result of acoustic reflections at the transmit and receive transducers. These reflections create persistent acoustic energy in the tissue in the form of a standing wave between the transducers at steady state. The standing wave can have a very significant impact on the acoustic impedance looking into the acoustic cavity formed between the transducers and, at specific frequencies, can result in improved impedance matching between the transducer and tissue by making the cavity appear less stiff to the transducer than it would be in the absence of the standing wave. At other frequencies the standing wave can worsen the impedance match by making the cavity appear stiffer to the transmit transducer. This frequency variation is the source of the frequency dependence of the PTE and impedance characterized by minima and maxima that are periodic with frequency.

In a subdermal implant, the acoustic separation distance between the external and implanted parts of the power link is expected to vary considerably between patients, and will also change with patient movement, hydration, and tissue growth. This sensitivity cause large swings in efficiency and represents a serious limitation on battery life and overall device reliability. Thus, techniques are needed to either passively reduce the dependence of transfer efficiency on separation or to actively compensate for changes in separation distance. There has not yet been a reported UTET system that performs real time compensation for separation distance changes in order to maximize power transfer efficiency.

SUMMARY

Methods are described herein that compensate for changes in separation distance between transducers. Methods are also described herein that reduce the dependence of transfer efficiency on separation. Methods are also described herein that determine when a receive transducer is fully charged. UTET systems are also described that incorporate one or more of these methods.

In general, in an aspect, a method of improving transfer efficiency is disclosed for a power link having a send transducer and a receive transducer and configured to transmit at a transmit frequency. The method includes detecting changes in inter-transducer separation and adjusting the transmit frequency. Implementations may include one or more of the following. The transmit frequency is adjusted by reference to changes in impedance phase as seen by the send transducer. The transmit frequency is selected by means of a lookup table. The transmit frequency is selected by scanning discrete frequencies and setting the transmit frequency to that frequency that is at an extremum closest in value to fopt for the send transducer.

In general, in an aspect, a method of dynamic charging in a power link is disclosed, the method including detecting a change in an electrical impedance during charging and discontinuing the charge upon detection of the change.

In general, in an aspect, a method of dynamic charging in a power link having a transmit unit and a receive transducer is disclosed, the method including changing an electrical load impedance as seen by the receive transducer, such that the transmit unit detects that more power is needed.

In general, in an aspect, a method of maintaining high power transfer efficiency is disclosed for a power link having a send transducer and configured to transmit at a transmit frequency. The method includes the steps of periodically scanning the transmit frequency through a range of discrete frequencies; digitizing current and voltage waveforms from the power link at each discrete frequency; integrating, digitizing, and calculating impedance phase at each discrete frequency; and setting the transmit frequency to the discrete frequency having an impedance phase extremum closest to $f_{opt}$ for the send transducer.

In general, in an aspect, power link UTET systems are disclosed that have circuitry and/or software that implement one or more of the above methods.

These and other features and aspects, and combinations of them, may be expressed as methods, systems, components, means and steps for performing functions, business methods, program products, and in other ways. Other advantages and features will become apparent from the following description and from the claims.

DESCRIPTION

FIG. 1 shows a schematic example diagram of an ultrasonic transcutaneous energy transfer/power link as if viewed along a section of tissue.

FIG. 2 shows an example measurement of the impedance magnitude and phase of a transducer in air (solid lines) and the impedance looking into the transmit side of a set of transducers in a power link configured as in FIG. 1, coupled through 6mm of water (dashed lines). The closely separated features in impedance for the coupled case arise due to acoustic resonances in the tissue while water damping has pushed the series resonant frequency lower.

FIG. 3 shows an example measurement of the impedance phase for coupled transducers through water in a power link configured as in FIG. 1, along with the measured power transfer efficiency (dashed and solid lines respectively). Local efficiency maxima are observed to lie in close proximity to the channel resonances. At the center of the plot the local efficiency maxima occur in close proximity to the minima of impedance phase.

FIG. 4 shows UTET PTE and impedance phase in a power link configured as in FIG. 1, separated by 5.9 mm and 6.1 mm of de-ionized water (solid and dashed lines respectively). The receive transducer was connected to a 940Ω load resistance. Arrows indicate the direction the peaks move when the separation distance is increased.

FIG. 5 shows a scatter plot of local maxima in a UTET over a range of separation distances spanning 3.0 mm to 7.0 mm. The vertical line denotes the global efficiency maximum $f_{opt}$ for this example UTET system.

FIG. 6 shows a block diagram of a feedback loop used in some Examples to adjust the transmit frequency based on the measurement of impedance phase, looking into the transmit side. The two comparators in the diagram, along with the XOR logic gate, and RC filter make up the phase measurement block. Neither measurements nor communication are needed on the receive side.

Figure 9:
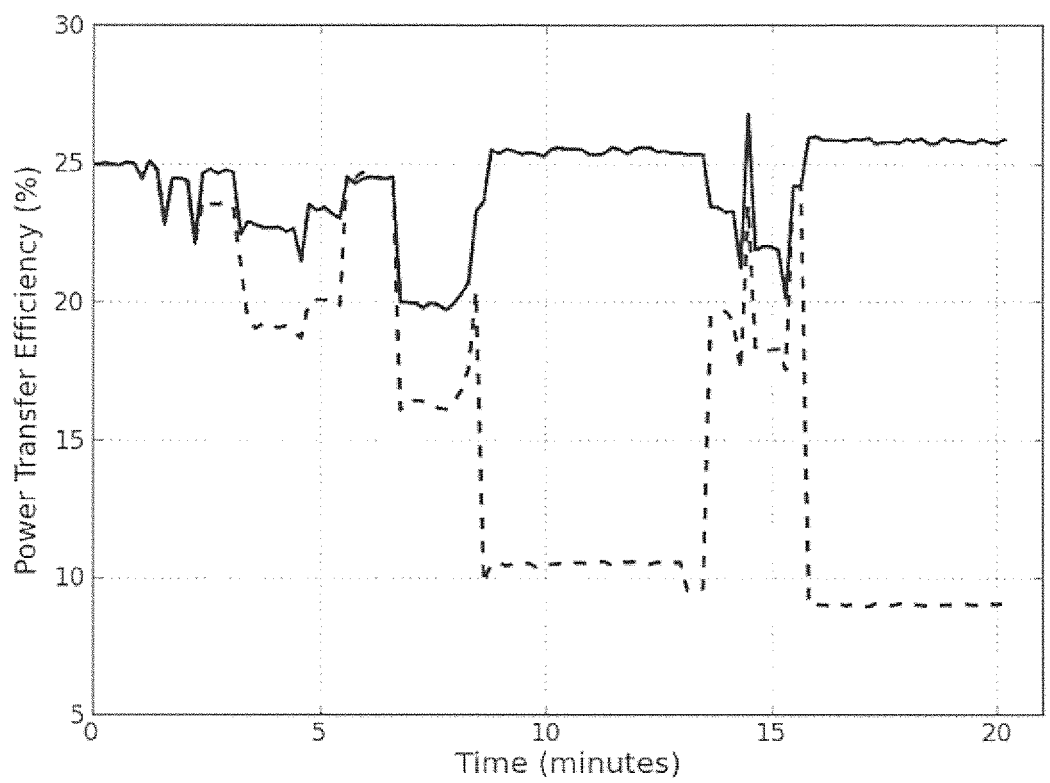

FIG. 9 shows the PTE achieved through a 5 mm porcine skin sample over time with a fixed transmit frequency and a frequency adjusted according to the steps in Table 1 (dashed and solid lines respectively). Random palpation events were applied to the sample by the experimenter leading to the changes in PTE. The receive side transducer was connected to a 940Ω load resistance.

Figure 10:
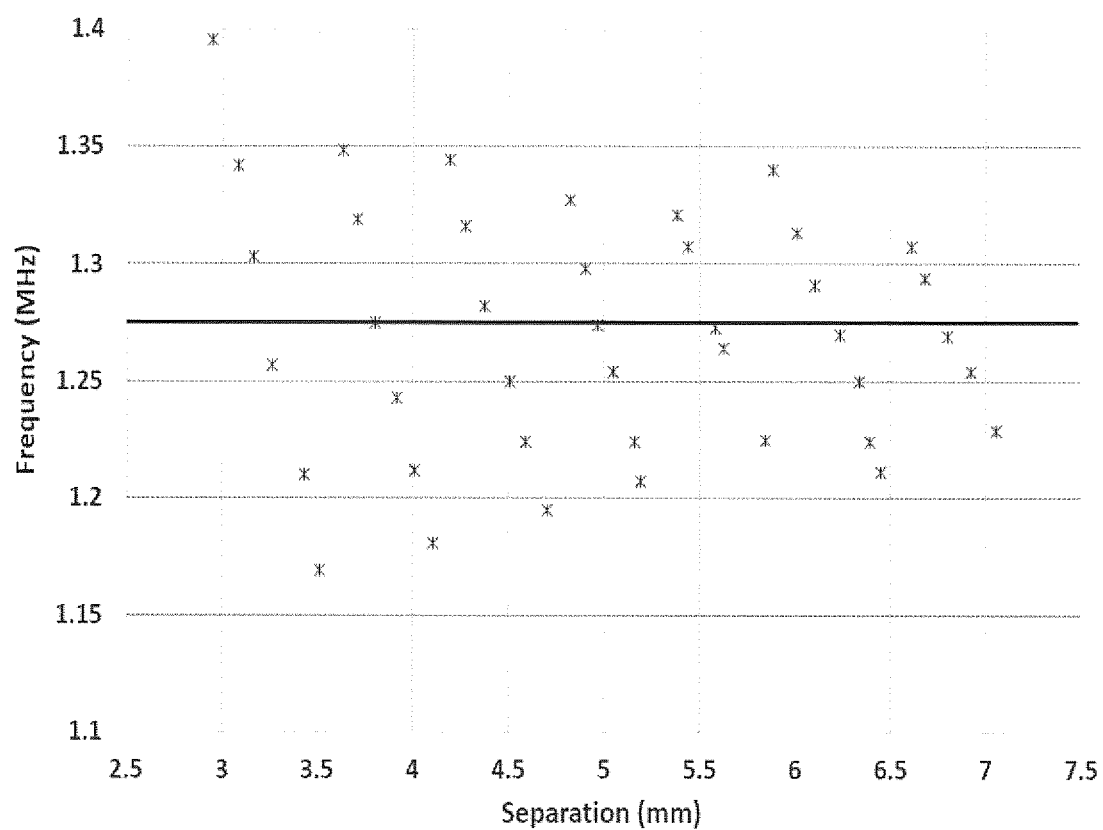

FIG. 10 shows measured optimal channel resonant frequency versus separation distance for a UTET system in de-ionized water. The center frequency for the piezoelectric transducers for an example UTET system, $f_{opt}$, is shown as a solid line.

Figure 11:
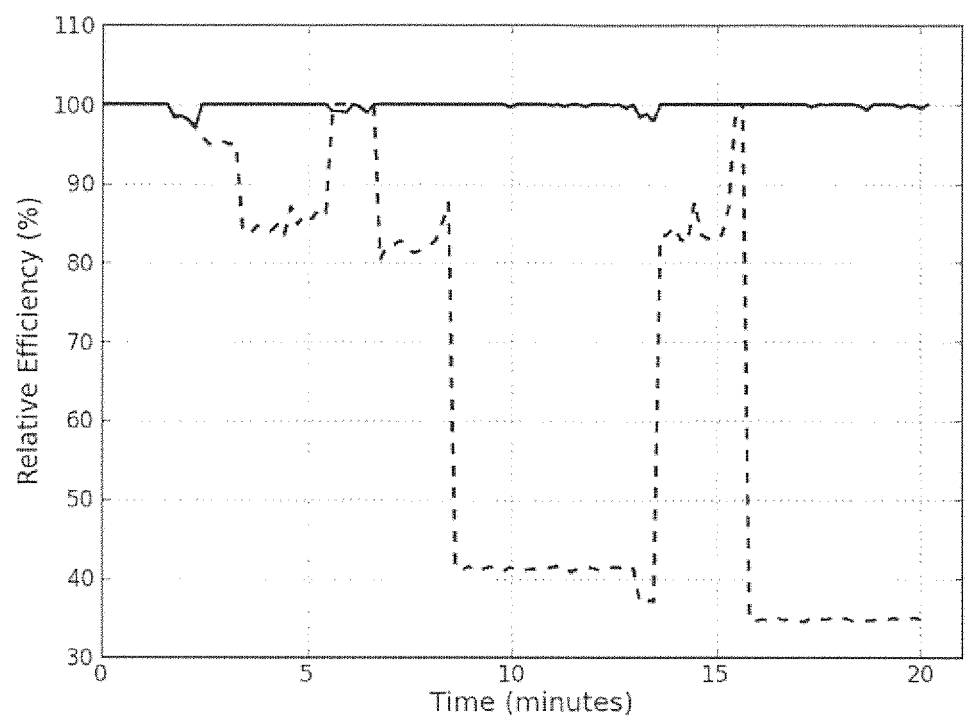

FIG. 11 shows a comparison of the drop in efficiency relative to the potential maximum when using frequency compensation (solid line) and a fixed transmit frequency (dashed line) for Example 1 below. The receive side transducer was connected to a 940Ω load resistance.

Figure 12:
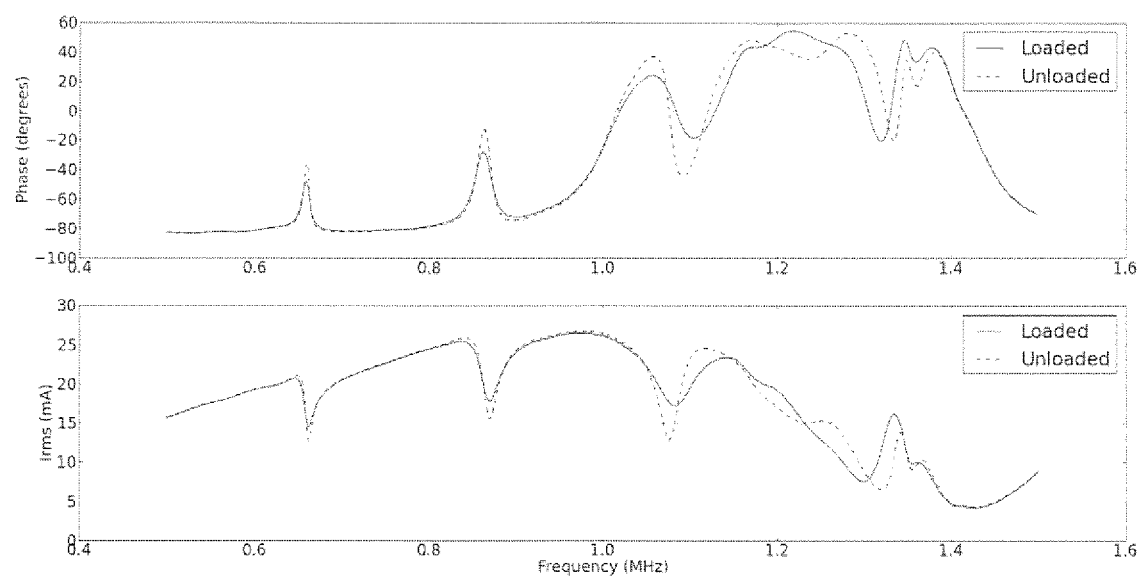

FIG. 12 shows impedance phase and RMS current for a transmit transducer coupled through water to a loaded (solid line) or an unloaded receiver (dotted line) as configured in Example 2.

Figure 13:
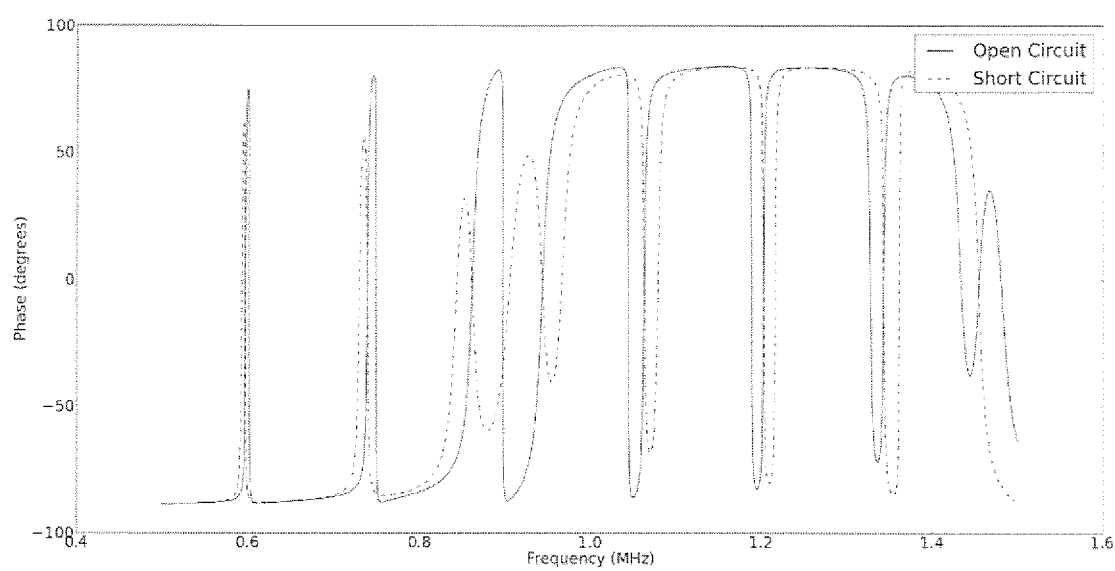

FIG. 13 shows a KLM simulation of the electrical impedance seen by a transmit transducer coupled to a receiver that has its terminals open circuited (solid line) or when a very small (R=1Ω) electrical impedance is placed across the device ("short circuit", dotted line).

PARTS LEGEND

101 Transmit side, send side
103 Tissue
105 Receive side
107 Send transducer, transmit transducer
109 Power source, external driver
111 Receive transducer
113 Electrical load A UTET system or "power link" includes a send unit that is external and a receive unit that is not physically coupled to the send unit, that when installed is separated by a distance from the send unit and imparts energy from the send unit to the receive unit across a medium. In some embodiments, the medium is air. In some embodiments, the medium is water. In some embodiments, the medium is mammalian tissue, preferably soft tissue. In some embodiments, the receive unit is implantable in a mammal. Methods are described herein that may be used to compensate for inter-transducer separation distance in a UTET system. In some embodiments, a method includes detecting changes in inter-transducer separation and adjusting the transmit frequency to deliver maximum PTE. In some embodiments, a method includes detecting changes in inter-transducer separation and adjusting impedance phase to deliver maximum power transfer efficiency. In some embodiments, impedance phase measurements and active frequency compensation are both adjusted. In some embodiments, this adjustment is actively managed in real time.

The frequency compensation strategy described herein can be implemented in low power and/or non-invasively. In some embodiments, only transmit-side measurements are needed. In some embodiments, no communication is required between external and implanted units. In some embodiments, few additional components are required. In some embodiments, a UTET system utilizing this method is suitable for use in wearable battery-operated systems. In some embodiments, a UTET system utilizing this method is suitable for use in the charging of portable electronic devices such as mobile phones. In some embodiments, a UTET system utilizing this method is suitable for us in battery-powered active implantable medical devices.

In some embodiments, use of the methods to improve transfer efficiency described herein results in higher and/or more consistent power transfer efficiency. In a benchtop UTET system we experimentally show (see Examples below) that without compensation, efficiency can range from 8% to 25% as a tissue sample is being manipulated to simulate in situ implant conditions. When active frequency compensation is implemented, the efficiency stays uniformly high, over 20% throughout. Using such a method, near-constant power transfer efficiency levels are maintained, even while tissue undergoes unpredictable changes in acoustic properties.

Additionally, in some embodiments, a method described herein includes determining when the receiver's energy storage element (e.g., re-chargeable battery, capacitor, etc.) has received enough charge from the external unit. This ability would allow energy saving on the external unit and subsequently extends the time between required battery changes. See Example 2 below.

By "ultrasound" or "ultrasonic", we mean energy imparted at a frequency of greater than approximately 20 kHz.

Figure 1:
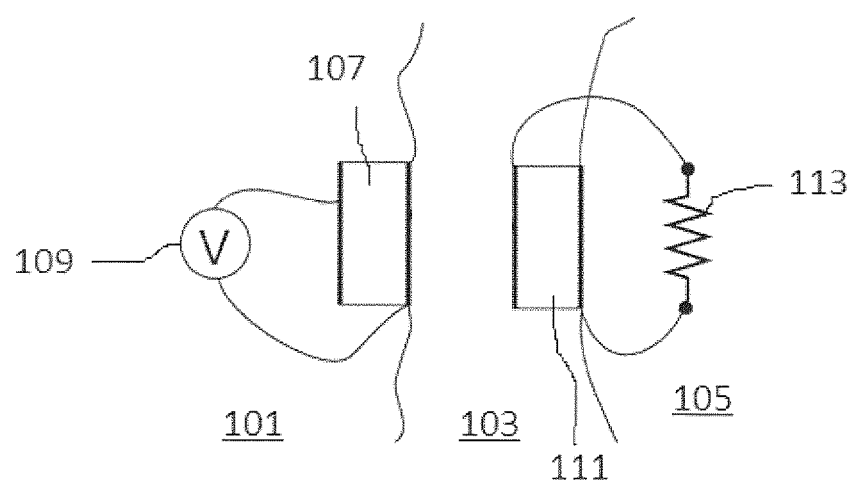

Illustration of a UTET system incorporating improvements in power transfer efficiency are shown in FIG. 1 with reference to an implantable medical device application. FIG. 1 shows an example UTET system for powering medical implants that comprises a piezoelectric transmit/send transducer 107 driven by an external driver 109; an amount of tissue 103 that ultrasonic energy must be transmitted through; and a piezoelectric receive transducer 111, preferably anchored to bone, and connected to an electrical load 113 (e.g., a medical implant). Preferably, a UTET system has high electromechanical coupling efficiency and low acoustic losses in the medium and in any backing or matching layers. The example system of FIG. 1 includes a transmit transducer driven by an electrical source and a receive transducer connected to an electrical load, $R_l$. The distance between transmit and receive transducer is a medium whose acoustic length can vary.

In some embodiments, methods of improving power transfer efficiency disclosed herein can be used to compensate for changes in the medium. In embodiments directed to implantable medical device applications, changes in the medium can be caused by variation in implant depths or acoustic changes caused by tissue changes such as growth, hydration, ambient temperature and movement.

UTETs can be characterized by their power transfer efficiency defined as:

$$\eta = \frac{P_{out}}{P_{in}} \quad (1)$$

where $P_{out}$ is the power delivered into a resistive load connected to the receive transducer and $P_{in}$ is the apparent electrical power supplied to the transmit transducer. $\eta$, $P_{in}$ and $P_{out}$ all exhibit a strong frequency dependence attributable to the coupled system response of the piezoelectric transducers and the tissue separating them.

Figure 2:
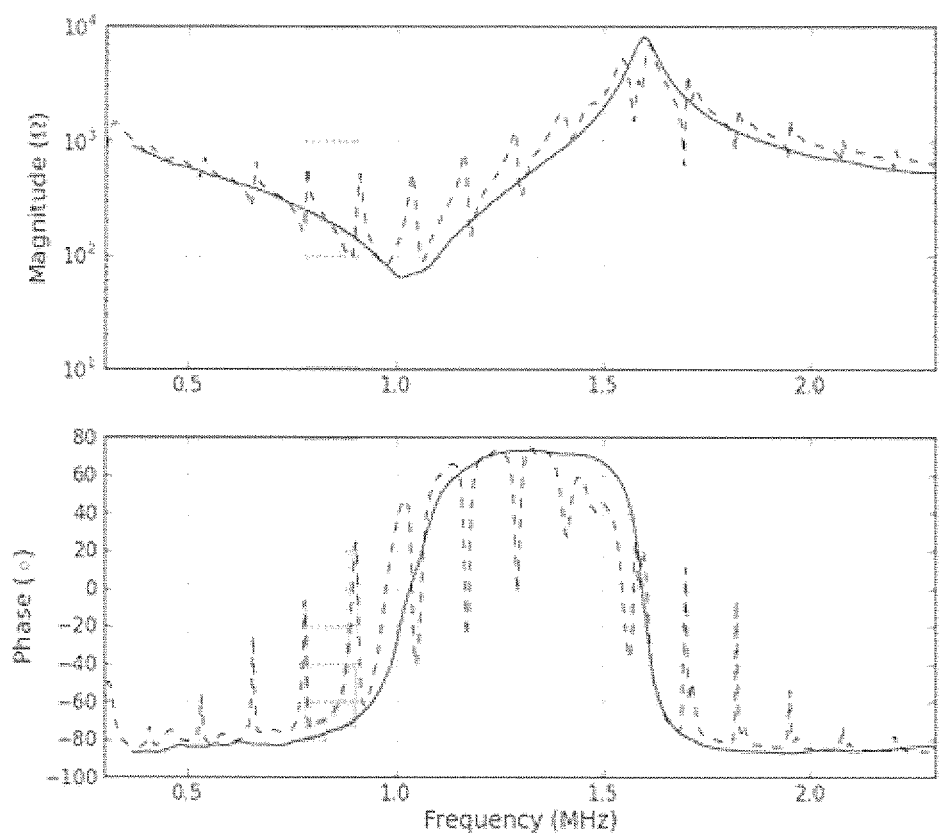
Figure 3:
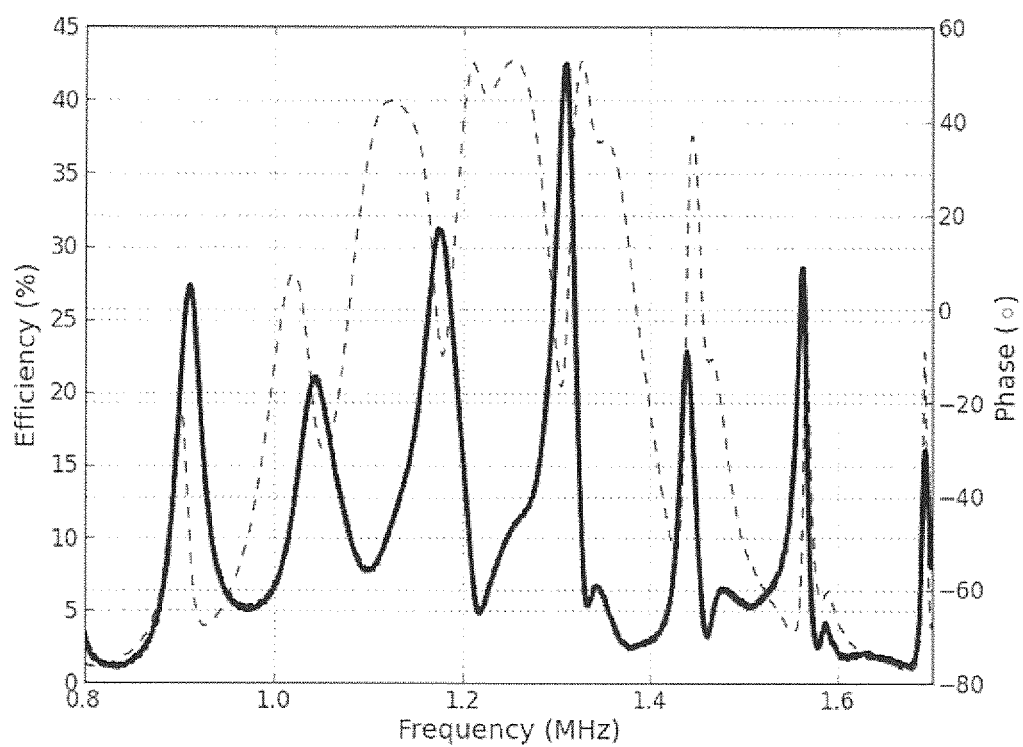

In some UTET systems, transducers emit sound at their fundamental frequency of a few 100 KHz to a few MHz, which is a common frequency range for balancing diffractive losses and tissue attenuation. For some sub-dermal implants, the separation between the transducers is typically on the order of 5 mm, while the ultrasonic wavelength is on the order of 1 mm. When considering transducers in the range of about 5 mm to about 15 mm diameter, the acoustic field generated is essentially one-dimensional. As a result, the tissue separating the transducers forms an acoustic cavity or transmission line with resonances occurring at frequencies separated by a frequency $\Delta f$ sufficient to allow an additional whole wavelength to fit in a cavity round trip distance. $\Delta f$ can therefore be calculated from:

$$\Delta f = \frac{c}{2L}. \quad (2)$$

where L is the length of the tissue between the transducers and c is the sound speed in the tissue. The periodic resonances spaced by $\Delta f$ give rise to periodic changes in the system response. For example, consider the impedance seen looking into a coupled transmitter receiver pair separated by 6 mm of deionized water shown in FIG. 2. The regularly spaced narrow impedance features shown are the acoustic resonances of the water channel, while the broad impedance features corresponds to the uncoupled transducer impedance shown by the solid line. These channel resonances also strongly modulate the transmission efficiency as shown in FIG. 3. It can be observed that not only is the periodicity of the resonances in the impedance phase and efficiency the same, but that in the central region of high efficiency the local maxima of efficiency correspond quite well with the minima of impedance phase.

In order for Equation 2 to hold, the two transducers must be in close enough proximity that they form a tightly coupled system in which acoustic energy is able to reflect between the transducers multiple times before being lost to diffraction or absorption. At frequencies around or below 1 MHz tissue absorption is 1 dB/cm or less, allowing multiple passes between transducers separated by a few millimeters. Diffraction effects will be small as long as the separation times the mean number of reflections between the transducers is smaller than the Fraunhofer distance—i.e. the distance at which the field pattern changes from a near-field to a far-field pattern. The Fraunhofer distance can be calculated from Equation 3 where D is the transducer aperture, $\lambda$ is the wavelength, and $d_f$ is the Fraunhofer distance. Transmitters and receivers can remain strongly coupled at distances of tens of wavelengths if the transducers diameter is large enough and absorption is weak.

$$d_f = \frac{2D^2}{\lambda} \quad (1)$$

The problem encountered in real-world application of UTETs for medical implants is that implant depth will vary across patients, and that both the speed of sound and tissue separation drift over a timescale of minutes to hours with motion, venous engorgement, temperature and hydration level and over longer timescales with tissue growth and weight changes. Fortunately, the separation of scales between the transducer response, which is on the scale of MHz and the tissue response, which has periodicity on the order of 100 KHz for a separation of a few mm in water or tissue, allows for a simple approach to tuning the operating frequency. If either c or L changes in Eq. 1, the frequency spacing between resonances is simply resealed and can be compensated for with a similar resealing in operating frequency. If the frequencies of maximum efficiency bear a fixed relationship to the channel's resonance frequencies, then a table of frequencies for maximum efficiency can be established for a particular set of c/L values. If a measurement is then able to track changes in c/L due to changes in tissue properties then the operating frequency can be adjusted to compensate, resulting in consistently high transmission efficiency.

Figure 4:
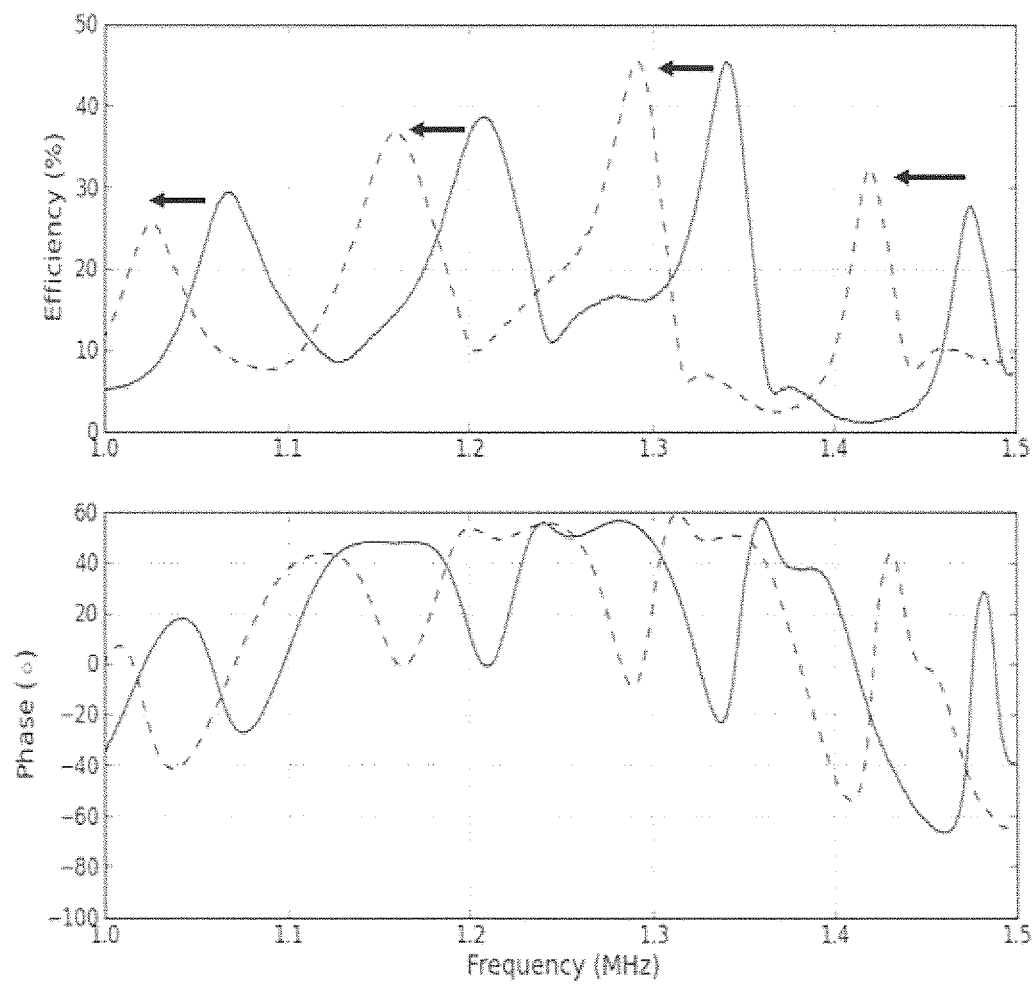

FIG. 4 shows the PTE and impedance phase spectra for two different water channel lengths, 5.9 mm and 6.1 mm. The spectra for the two different lengths are close to being frequency-shifted copies of each other, with some small changes in amplitude and a small change in the separation between adjacent resonance features.

In a fixed transmit frequency UTET system the shifts to the efficiency spectrum caused by separation changes can cause a very large reduction in PTE. However, if the transmit frequency were to be adjusted so as to track the shifting of the efficiency peaks, a consistently high efficiency could be maintained in the presence of unpredictable changes in acoustic separation.

Increasing the separation between the two transducers has two effects. The spectral features associated with the resonance shift to lower frequencies and the resonance features become more closely spaced in accordance with Eq. 2. The frequency that has the absolute maximum efficiency will correspond to one of the channel resonances, i.e. to one of the local maxima in the efficiency spectrum, but it is also affected by the frequency dependence of the piezoelectric transducer response. The latter effect is not sensitive to changes in the separation distance since changes to the separation do not affect the transducers themselves.

Figure 5:
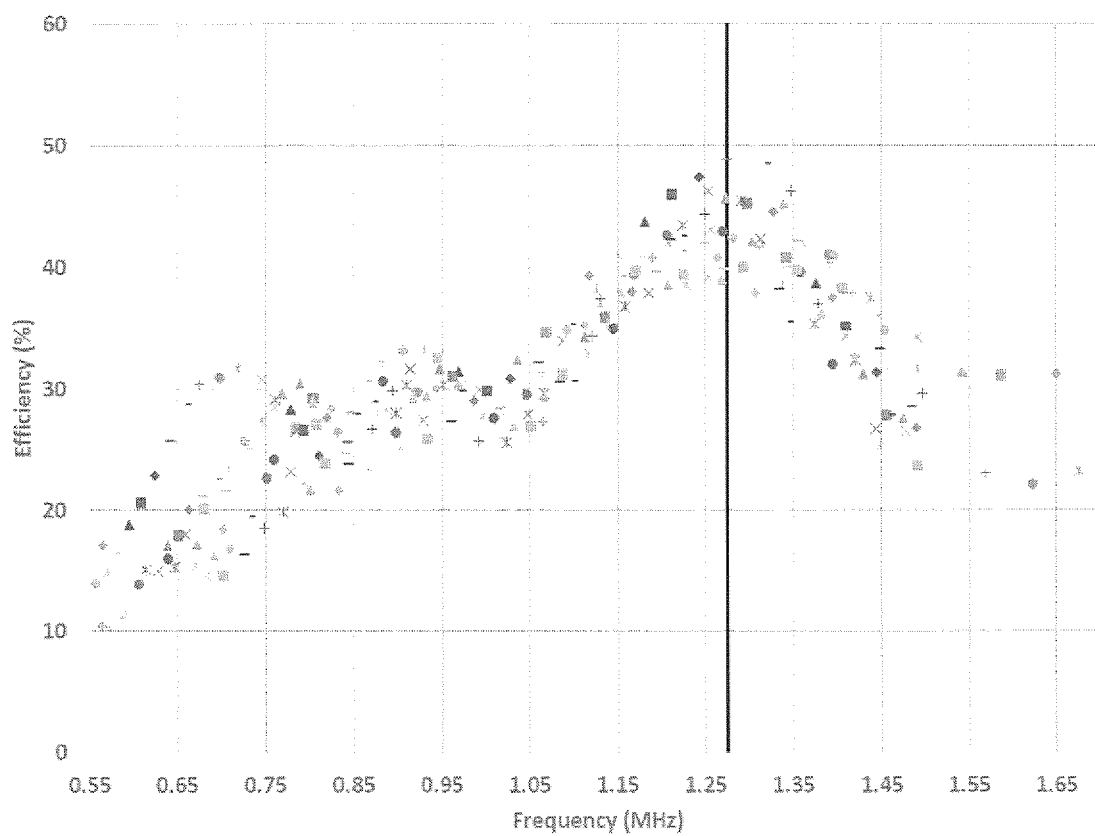

If the frequencies corresponding to local maxima in efficiency over a large range of separation distances spanning multiple wavelengths are plotted as a scatter plot we obtain a plot similar to FIG. 5. This plot shows that there is a global best operating frequency, characteristic to each transducer, which corresponds to the resonant frequency of the transmit transducer when damped by the acoustic load of the cavity and receive transducer. This frequency, marked by the solid vertical line in FIG. 5, is $f_{opt}$ for the particular transducer shown in FIG. 5. Resonances are also evident when inspecting the electrical impedance for the transmit transducer in a UTET system. The electrical impedance for a piezoelectric transducer can be characterized in air and shows one or more resonances associated with the geometry & material characteristics of the piezoelectric being used. When coupled across tissue with a receive transducer, additional resonances show up in both the magnitude and phase for the electrical impedance. These additional resonances in the impedance allow for a non-invasive method for tracking the ideal operating frequency for power transfer efficiency.

In some embodiments, the operating frequency is set at $f_{opt}$. In some embodiments, the operating frequency is set to one of a range of frequencies around $f_{opt}$ (e.g., for the system of FIG. 5, from about 1.15 to about 1.40 MHz). When a channel resonance is not coincident with $f_{opt}$, in some embodiments the link operates at the local efficiency maximum closest to $f_{opt}$ and still obtains a high efficiency.

While a 1D KLM model of the UTET predicts that the efficiency should be unchanged by increasing the separation of the transducer by integer multiples of a half wavelength (assuming zero attenuation in the water), the experimental data shows a spread in the efficiencies at any given frequency. This spread is likely due to 2D effects such as diffraction and to experimental errors in maintaining alignment as the transducers are separated (see C. Mo, S. Hudson, and L. J. Radziemski, "Effect of misalignment between ultrasound piezoelectric transducers on transcutaneous energy transfer," 2013, p. 868814; hereby incorporated by reference). Acoustic pressure field variation can cause phase shifts across a receive transducer that lead to varying degrees of voltage cancellation. This is a separate effect from the effects of separation distance on PTE.

Given the above discussion there are a number of different methods that could be used to tune the operating frequency of a UTET system to compensate for changes in separation between the transducers. One approach is to keep track of input power and output power using external and implanted hardware while periodically sweeping across operating frequency. The ratio of these measurements would yield the efficiency spectrum directly making it straightforward to identify the frequency of maximum efficiency. However, this approach requires additional implanted electronics and a communication link between the implant and external unit which can be cumbersome if it is not already available in the design. While it would be possible to continuously monitor transmit and receive power in order to directly calculate the efficiency in the system, such an approach requires measurements in both the external and implanted units and a communication link between them.

An approach that relies only on measurements performed on the transmit side is preferable, so that no communication is needed to keep the transmitter at the optimal frequency. To implement such a solution, note that the impedance seen looking into the transmit transducer exhibits the same periodic frequency dependence as the efficiency. In some embodiments, a measurement of the impedance from the transmit side can be used to rescale the transmit frequency to achieve maximum efficiency. This method is based at least in part on the finding that the minima of the transmitter's impedance phase lie quite close to the maxima of efficiency, particularly for frequencies near $f_{opt}$.

Figure 6:
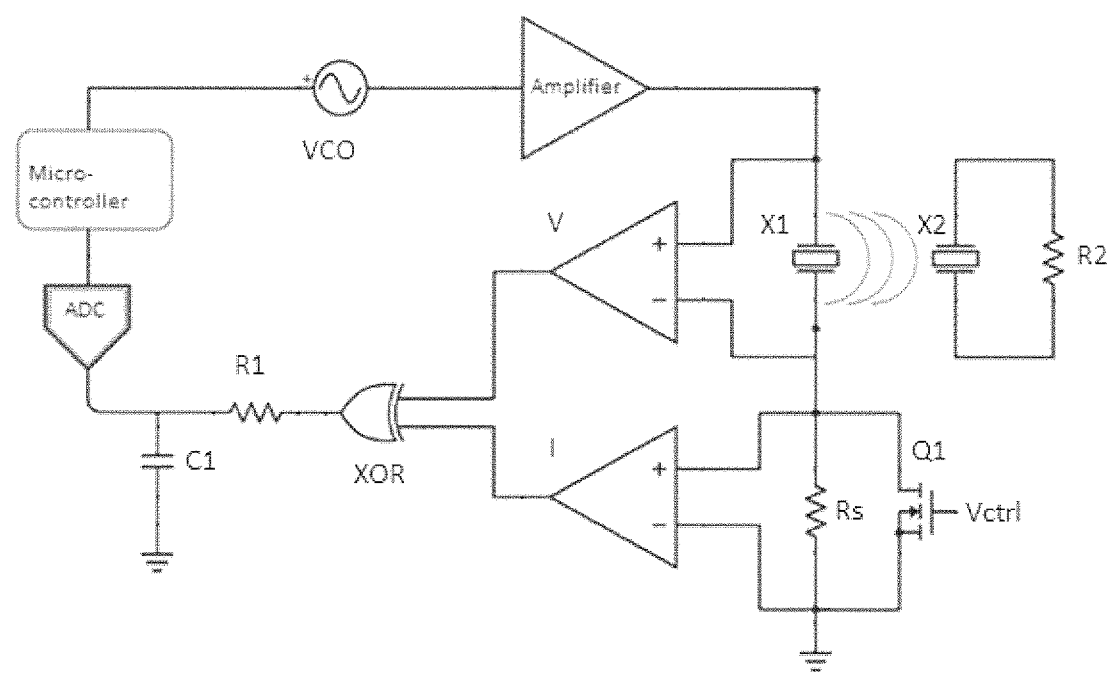

A diagram of a-closed loop feedback system that can be used to control the transmit frequency is shown in FIG. 6. In this circuit a measurement of impedance is performed on the transmit side by sweeping the drive frequency over a range chosen to cover multiple resonances in the acoustic channel centered around a nominal separation distance chosen for the system. The resonances can be readily identified in the real and imaginary parts of the impedance as well as in the phase and magnitude. It is only necessary therefore to measure one of these quantities in order to detect changes in c/L. Impedance phase is a convenient measurement to use since it can be made with a relatively simple, and low-power circuit involving comparators and a digital phase detector. Such a circuit, such as the one shown in FIG. 6, can be implemented using low-powered CMOS logic devices, which is important for battery-operated biomedical devices. A low-sampling rate analog-to-digital converter and microcontroller are also used to measure the impedance phase at each frequency, determine where the minima occur and adjust the transmit frequency as needed to track the maximum efficiency frequency. Once the operating frequency is determined, transistor Q1 in FIG. 6 can be enabled to bypass the current sense resistor, Rs, eliminating power dissipation. The comparators can be put into shutdown mode and only woken up when an impedance phase measurement needs to be made.

Measurement of the impedance phase can be evaluated by comparing the location of zero-crossings in the current and voltage waveforms using a standard phase detector digital logic circuit, which can be implemented with low-powered CMOS logic devices. FIG. 3 shows the simultaneous measurement of impedance phase looking into the transmit side of a pair of coupled UTET transducers and the power transmission efficiency of the pair. It can be observed that not only is the periodicity of the resonances in the impedance phase and efficiency the same, but that in the central region of high efficiency the local maxima of efficiency correspond quite well (although not exactly) with the minima of impedance phase. This close correspondence between the efficiency maxima and phase minima results from the use of transducers without a matching layer. When matching layers are put on the transducers, a non-negligible shift can be observed between the frequency of. maximum efficiency and the frequency of minimum impedance phase in the high-efficiency portion of the impedance curve. However, the shift is consistent between pairs of impedance phase minima so that if the efficiency peak occurs 20% of the way between two impedance phase minima for one pair of phase minima, it will also occur 20% of the way between the next pair of phase minima. This has been observed in both experimental data herein and in simulations using a 1D KLM-style model. As a result of this periodicity over a large range of operating frequencies, it is possible to generate a lookup table of calibration impedance and efficiency data from experimental measurements performed once on a UTET system.

During subsequent operation acoustic changes in the tissue properties may rescale c/L, but in some embodiments, impedance phase is measured to obtain the scaling factor relative to the reference data. This allows the reference efficiency data to also be rescaled and for the optimal operating frequency to be predicted for the current state of the tissue. In some embodiments, a general algorithm for undertaking this operation is:

1. Step the transmit drive frequency through N discrete frequencies 1.1 At each frequency perform 1-bit digitization of current and voltage waveforms with a comparator
1.2 Calculate impedance phase using a phase detector on the digitized current and voltage waveforms
1.3 Integrate and digitize the impedance phase at each frequency and store results in a microcontroller
2. In the resulting impedance phase vector locate the frequencies at which the impedance phase minima and maxima occur using threshold comparisons
3. Make a correspondence between the measured phase minima and maxima and a set of previously measured reference phase minima and maxima
4. Use a lookup table to find the percent distance between the local impedance phase extrema and the local maximum in efficiency in the reference data
5. Calculate the frequency which is the same percent of the way between the frequency in the measured data as the efficiency maximum is between the corresponding extrema in the reference data.
6. Set the drive frequency to the frequency calculated in 5.

In embodiments without matching layers, where there is good correspondence between frequencies of minimum phase and frequencies of maximum efficiency, the algorithm may be simplified; steps 4-6 would then be unnecessary and the frequency of minimum phase with the highest corresponding efficiency in the reference data can be set as the drive frequency.

To further characterize the frequency tuning range, a water bath experiment was performed where the separation between UTET transducers was increased from ~3.0 mm to ~7.0 mm; see FIG. 10. It can be seen in this Figure that as the separation increases the frequency of maximum efficiency generally moves from high frequencies to lower ones, but at a certain point a new higher frequency becomes the new frequency of maximum efficiency causing a discontinuity in the curve. Over the full measured range of separation distances the frequencies of maximum efficiency are symmetrically distributed about $f_{opt}$, so that a good strategy at any separation is to operate at the local efficiency maximum that lies closest in frequency to $f_{opt}$. Since $f_{opt}$ is a property of the transducers, not of the medium separating them, it only needs to be measured once as part of an initial calibration. Such a calibration would measure the efficiency at each channel resonance over a range of transducer separations in a water bath, producing a scatter plot as in the Figures herein. $f_{opt}$ is determined as the location of the maximum in the curve and can be stored in non-volatile memory on the microcontroller.

As such, in preferred embodiments, the steps for maintaining maximum power transfer efficiency in a UTET system are as follows:
1. Step the transmit drive frequency through N discrete frequencies
   1.1 At each frequency perform 1-bit digitization of current and voltage waveforms with a comparator
   1.2 Calculate impedance phase using a phase detector on the digitized current and voltage waveforms
   1.3 Integrate and digitize the impedance phase at each frequency and store results in a microcontroller
2. Find the local extrema in the measured impedance phase
3. Set the drive frequency to the impedance phase extremum closest to the system's global optimum frequency ($f_{opt}$)

For values of transducer separation corresponding to the sharp increases in frequency in FIG. 10 it is possible for there to be two extrema of phase impedance that are equidistant from $f_{opt}$. If this is the case the two frequencies will have nearly identical efficiencies and so it does not matter which of the two is selected for the transmit frequency.

The algorithm may be repeated as often as needed to compensate for tissue changes. We estimate that executing the algorithm every few minutes should be adequate to compensate for changes likely to be seen in applications like cochlear implant powering. The time-averaged power draw associated with tracking the optimal frequency is likely to be small. For the UTET system examined in the Examples, changes as small as $\frac{1}{30}^{th}$ of a wavelength resulted in changes in power transfer efficiency of >5%. As such, in preferred embodiments the algorithm is executed whenever potential tissue changes could exceed about 30 microns, or about 20 microns, or about 10 microns.

In some embodiments, the power link is constructed according to the instuctions given in PCT/CA2014/050436, hereby incorporated by reference. In some embodiments, a power link equipped to perform automatic frequency adjustment comprises 1) a frequency tunable amplifier driving the transmit side of an ultrasonic link, 2) an impedance phase measurement circuit, 3) a microcontroller, and 4) an analog to digital converter. Within (3), the ideal operating frequency is stored in memory and is known for the piezoelectric transducer pair being used. A frequency sweep is can then be performed while monitoring the impedance phase using (2) and (4). The frequency locations for each channel resonance are then known and compared to the known ideal frequency. Finally, the amplifier driving the UTET system (1), is set to the frequency closest to $f_{opt}$ that satisfies the resonance condition.

The methods described above work well when the tissue channel length corresponds well with the center frequency of the transducers. In some embodiments, the methods include detection of cases in which channel resonances occur outside of the operating range of the transducer. In some embodiments, the methods include detection of cases in which acoustic cavity resonances become closer together, minimizing the coarse tuning range that is required. In some embodiments, the absolute maximum efficiency value is found and the power link is configured to operate at the nearest local minima in phase reflecting the closest channel resonance.

The following publications are incorporated by reference in their entirety Jeff R. Crandall, Barry S. Meyers, David F. Meaney, and Salena Zellers, "Pediatric Injury Biomechanics", Springer Science+Business Media New York 2013, pp. 183-184; S. Q. Lee, W. Youm, and G. Wang, "Biocompatible wireless power transferring based on ultrasonic resonance devices," Proc. Acoustical Society of America Symposium, Vol. 19, pp. 030030, 2013; D. Shmilovitz, S. Ozeri, C.-C. Wang, and B. Spivak, "Noninvasive Control of the Power Transferred to an Implanted Device by an Ultrasonic Transcutaneous Energy Transfer Link," IEEE Trans. Biomed. Eng., vol. 61, no. 4, pp. 995-1004; J. Leadbetter, J. A. Brown, and R. Adamson, "The Design of Ultrasonic Lead Magnesium Niobate-Lead Titanate (PMN-PT) Composite Transducers for Power and Signal Delivery to an Implanted Hearing Aid," Proc. Acoustical Society of America Symposium, Vol. 19, pp. 030029, 2013; S. Ozeri and D. Shmilovitz, "Ultrasonic transcutaneous energy transfer for powering implanted devices", Ultrasonics, 50, 556-566 (2010); F. Figueroa and E. Barbieri, "An Ultrasonic Ranging System for Structural Vibration Measurements," IEEE Trans. Instrum. Meas, vol. 40, no. 4, August, pp. 764-769, 1991; D. Leedom, R. Krimholtz and G. Matthaei, "Equivalent circuits for transducers having arbitrary even-or-odd symmetry piezoelectric excitation," IEEE Trans. Sonics Ultrason., vol. SU-18, pp. 128 -141, 1971.

Utility of the methods and power links described herein are further illustrated in the following Examples:

EXAMPLE 1

We implemented a frequency tracking PTE method as described above in a benchtop system consisting of a matched pair of air-backed PMN-PT (32%) 1-3 composite transducers with 8 mm diameter and 1.2 mm thickness. The bulk PMN-PT was sourced from Omega Piezo Technologies, State College, Pa. and had an electromechanical coupling of 0.54-0.60, a frequency constant of 2260 Hz-m, a mechanical quality factor of 80, and a material density of 8.2 g/cm$^3$; once fabricating using a dice and fill methodology as described in W. A. Smith and B. A. Auld, "Modeling 1-3 composite piezoelectrics: thickness-mode oscillations," IEEE Trans. Ultrason. Ferroelectr. Freq. Control, vol. 38, no. 1, pp. 40-47, Jan. 1991 (hereby incorporated by reference), the bulk piezoelectric material was made into a 1-3 composite transducer with kerfs filled with Epotek 301 epoxy. Making the bulk material into a composite increased its electromechanical coupling coefficient from 0.61 to 0.80.

Figure 7:
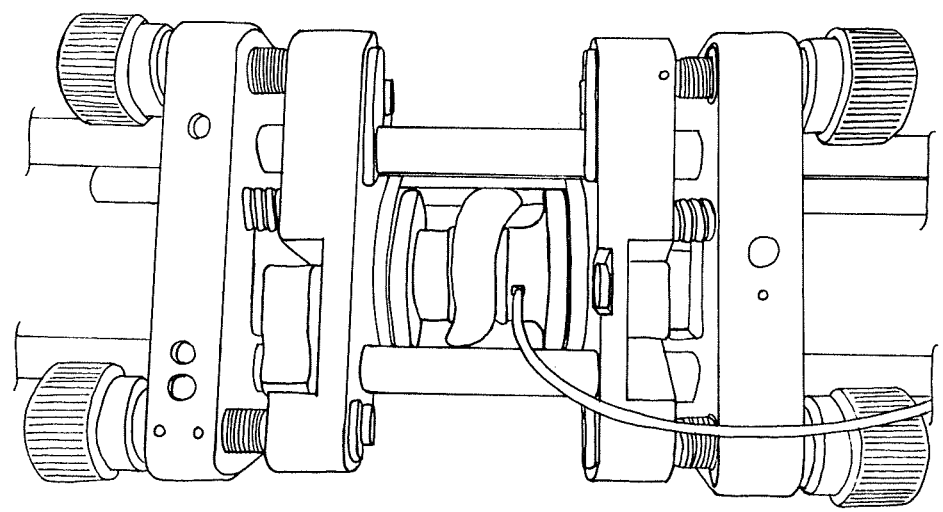
FIG. 7 shows a photograph of the experimental setup in Example 1. A porcine tissue sample is sandwiched between two transducers on kinematic mounts in a cage mount system.
Figure 8:
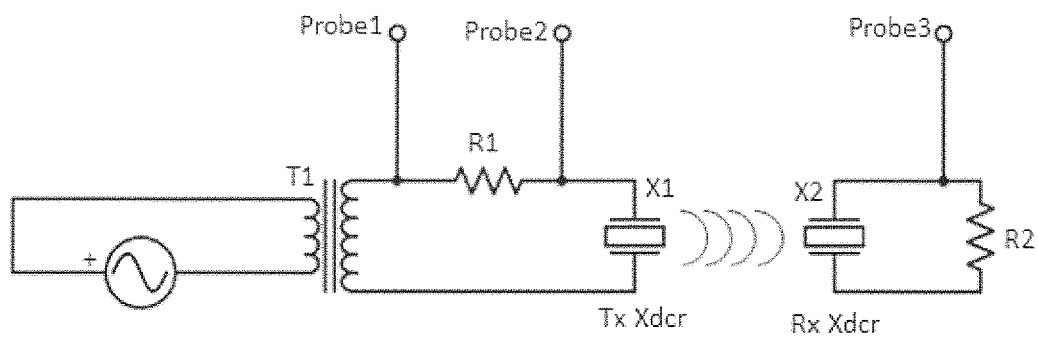
FIG. 8 shows a schematic for circuit connections in Example 1. R1 is the sense resistor, T1 is the transformer, and R2 is the matched load resistance.

The series resonance and parallel resonances of the transducers were measured in air to be 1.016MHz and 1.596 MHz respectively. The frequencies between the two transducers were matched to within <5%. The transducers were air-backed with no matching layer on the front side and capable of achieving a maximum electrical-to-electrical efficiency of 45% through a 2 mm deionized water gap. The transducers were mounted on two 3-axis cage-mount kinematic stages (Thorlabs, Newton, N.J.) so that angle and separation distance could be easily adjusted. Experiments were conducted through a porcine skin tissue sample with a thickness of 5 mm (composed of ~2 mm of epidermis and dermis and ~3 mm of subdermal fat). The entire assembly was submerged in a water bath for testing. A photograph of the experimental setup is shown in FIG. 7 and FIG. 8 shows the circuit connections. Efficiency measurements were evaluated under two conditions. In the first condition the frequency of maximum efficiency was determined at the start of the experiment and the transducer link efficiency was continuously evaluated at that static operating point. In the second condition, the impedance phase looking into the transmit transducer was monitored and the transmit frequency was chosen using the $f_{opt}$ related steps given above. Every five seconds the efficiency under each condition was measured, and during these measurements the tissue between the UTET transducers was manually manipulated in order to induce changes in effective acoustic length.

Tissue manipulations consisted of random palpations applied by the operator. As can be seen in FIG. 9, the palpation events were observed to cause large fluctuations in the PTE when the transmit frequency was held fixed (dashed line). Efficiency for the fixed transmit frequency dropped as low as 8% from its initial value of 25%. In contrast, when the transmit frequency was adjusted according to the steps as described above, the efficiency remained above 20% over the course of the 20 minute experiment. It will be noted that that transmit frequency adjustment does not completely eliminate variation in PTE with tissue length. Partly this is because there is some variation in efficiency due to detuning of the transmit frequency from $f_{opt}$. It is also partly due to the tissue manipulation causing angular or lateral misalignment, changes in tissue absorption, reflectance or other effects that reduce efficiency but cannot be compensated by adjustments in frequency.

In order to remove these effects from the analysis the efficiencies can be compared to the maximum efficiency that can be achieved at a given moment in time as measured from the complete efficiency spectrum. FIG. 11 shows the same data normalized to the maximum achievable efficiency. The efficiency obtained by executing this method remains within >97% of the maximum possible PTE while the fixed frequency system fluctuates strongly, reaching a worst-case value that is only 34% of the potential maximum.

The transmit transducer was driven from the 50 ohm output of an Agilent 33210A (Agilent, Santa Clara, Calif.) function generator. A transformer was used to increase the drive voltage to the piezoelectric device and a sense resistor, Rsense=209Ω, was used to monitor input current. Voltage signals were observed using an Agilent DS06014A oscilloscope. Both the voltage and current waveforms allowing for complex impedance to be determined over the desired frequency range. All instruments and calculations were controlled using custom scripts written in Python.

The input power was calculated as:

$$P_{in} = |V_{in} I_{in}^*| \tag{4}$$

where $V_{in}$ and $I_{in}$ are the complex input voltage and current. The receive transducer was connected to a $R_{load}$=940Ω resistive load selected as the closest real load match to the receive transducer output impedance at $f_{opt}$. The voltage across the load was measured with the oscilloscope. The load power was calculated as:

$$P_{out} = \frac{|V_{out}|^2}{R_{load}} \tag{2}$$

The link efficiency was calculated according to Eq.1 at each frequency from 1.25 MHz to 1.35 MHz stepping in 5 K.Hz steps.

The experimental results show that it is possible to maintain a uniformly high efficiency in a UTET system by continuously monitoring impedance phase and adjusting the operating frequency of the system based on that measurement. Both fast and slow tissue changes can be accounted for (mimicking in situ conditions like motion, and tissue growth respectively).

Our experiments were conducted using a fixed resistive load for simplicity. A more realistic system for ultrasonic power transfer would present a complex conjugate load in order to maximize power transfer from the receive transducer. However, there is no simple way of providing a complex conjugate load in a frequency-independent manner, and so a fixed resistive load offers a reasonable measurement condition. In some embodiments powering an implant, the load may be time-varying and complex and additional receive-side circuitry will be needed to drive it in an efficient manner.

The experiment described here made use of piezoelectric transducers with no matching layers. Matching layers can be used to improve coupling to water which tends to reduce the drop in efficiency for frequencies away from the cavity resonances. However, unless both the matching and electromechanical coupling are perfect (which is not possible in a practical system), resonances will still affect efficiency and so frequency tuning can still provide benefits in such systems. While the experimental results described here are for a specific transducer design, the approach of tuning transmit frequency to compensate for changes in tissue applies to any UTET system in which the two transducers are tightly coupled.

EXAMPLE 2

Dynamic/On-demand Charging

The impedance phase looking into the transmit transducer is observed to vary significantly depending on the load that is connected to the receiving transducer. In some embodiments, a buck or boost converter is implemented on the receive side of an ultrasonic power link, which has the capability to dynamically turn on and off in response to the status of a storage element. See FIG. 12. In an ultrasonic link, it is also possible to use electrical impedance in order to achieve dynamic/on-demand charging. Using the implanted piezoelectric device, the impedance seen by the transmitting piezoelectric element can be modulated by altering the load connected to the receiver. See FIG. 13. In some embodiments, a change in resonance locations can be used as an indication to the transmitter when charging is required.

In some embodiments, the presence/absence of impedance modulation is a binary indication for the transmitter of the internal charge state. In some embodiments, the indication can also be used to convey other information if required.

In some embodiments, a phase measurement circuit on the transmit side of the link can be used for detecting the status of the boost converter and perform dynamic charging of the receive element. In some embodiments, the input current can be monitored for the transmitting unit as it is also affected by the load conditions of the receiver with the input current dropping when the load is disconnected from the receive side. A sense resistor can be used to monitor the DC current delivered to the transmitting amplifier in real-time in order to detect a charged state.

Either the change in impedance or the change in current can be used to detect a change in the load state corresponding to a charger circuit completing charging of a storage element. Detection of this change can be made to cause the transmit unit to stop transmitting power to the receive element. The transmitter can periodically poll the current or impedance into the link to determine whether the condition has changed and more power is required.

On the receive side, the receive charging controller can connect the receive transducer to a fixed load or a short circuit to indicate that charging is required. This impedance will be seen on the transmit side during polling and can be made to cause the transmitter to resume transmission.

The invention claimed is:

1. A method of improving transfer efficiency in an ultrasonic power link having a send transducer and configured to transmit at a transmit frequency, in which the send transducer has a fixed resonant global best operating frequency characteristic to the send transducer, the method comprising detecting changes in impedance phase as seen by the send transducer by sweeping the transmit frequency over a range of frequencies, identifying a target frequency at which the impedance phase is at a local minimum that is closest in value to the global best operating frequency, and adjusting the transmit frequency to the target frequency.

2. An ultrasonic power link having circuitry and/or software that implements the method of claim 1.

3. The ultrasonic power link of claim 2 in which the link has a receive side comprising a receive transducer; and a transmit side comprising a microcontroller having memory and a frequency tunable amplifier driving a send transducer, an impedance phase measurement circuit, and an analog to digital converter; wherein the frequency is set to the extremum closest in value to a global optimum frequency that is preselected for the send and receive transducers and is stored in the microcontroller memory.

4. A power link for ultrasonic energy transfer in which the link has a receive side comprising a receive transducer; and a transmit side comprising a microcontroller having a memory and a frequency tunable amplifier driving a send transducer that is configured to transmit at a transmit frequency, an impedance phase measurement circuit, and an analog to digital converter; wherein a global best operating frequency characteristic to the send transducer is preselected and stored in the microcontroller is preselected and stored in the microcontroller memory; wherein the microcontroller memory also has instructions for sweeping the transmit frequency over a range of frequencies; digitizing current and voltage waveforms from the power link for each frequency in the range of frequencies; integrating, digitizing, and calculating impedance phase for each frequency in the range of frequencies; identifying a target frequency at which the impedance phase is at a local minimum that is closest in value to a global best operating frequency, wherein the global best operating frequency is characteristic to the send transducer, and adjusting the transmit transducer frequency to the target frequency.

* * * * *